United States Patent [19]

Rossiter

[11] Patent Number: 5,920,385

[45] Date of Patent: *Jul. 6, 1999

[54] OPTICAL ENERGY TRANSFER METHOD

[76] Inventor: Val J. Rossiter, c/o AABSPEC, 3 Springfield Park, Foxrock, Dublin 18, Ireland

[21] Appl. No.: 08/891,847

[22] Filed: Jul. 10, 1997

Related U.S. Application Data

[60] Provisional application No. 60/021,521, Jul. 10, 1996.

[51] Int. Cl.[6] .............................. G01N 21/00; G01J 3/00; G01J 3/44; G01J 3/40

[52] U.S. Cl. ........................... 356/73; 356/300; 356/301; 356/302; 356/306

[58] Field of Search ............................. 356/73, 300, 301, 356/302, 306, 326, 436

[56] References Cited

U.S. PATENT DOCUMENTS

| | | | |
|---|---|---|---|
| 5,408,314 | 4/1995 | Perry et al. | 356/301 |
| 5,428,222 | 6/1995 | Alexay | 356/436 |

*Primary Examiner*—Frank G. Font
*Assistant Examiner*—Roy M. Punnoose
*Attorney, Agent, or Firm*—Sughrue, Mion, Zinn, Macpeak & Seas, PLLC

[57] ABSTRACT

A method of collecting optical energy which allows the use of short focal length mirrors of relatively small physical size and in particular the use of the standard collecting mirrors usually employed in such spectrophotometers, for a wide range of sample sizes and collection configurations. A relatively large diameter internal surface, which in many cases can be incorporated into the design of other elements in the sampling system, is used. A physically large cell is interfaced to a radiation collector, such as a mirror. In this case the nut sealing the end window on the cell is internally coated (with gold in the preferred embodiment) to constitute a surface and this acts as a transfer mechanism for the backs-scattered radiation from sample. A solid collecting angle of 60 degrees (in this example) can be so obtained to transfer the energy to the standard radiation collector, such as a collecting mirror, of the spectrophotometer. Radiation, such as laser light, incident upon the sample reflects off the internal optic transfer surface and so falls incident on a collecting mirror, or the like.

9 Claims, 1 Drawing Sheet

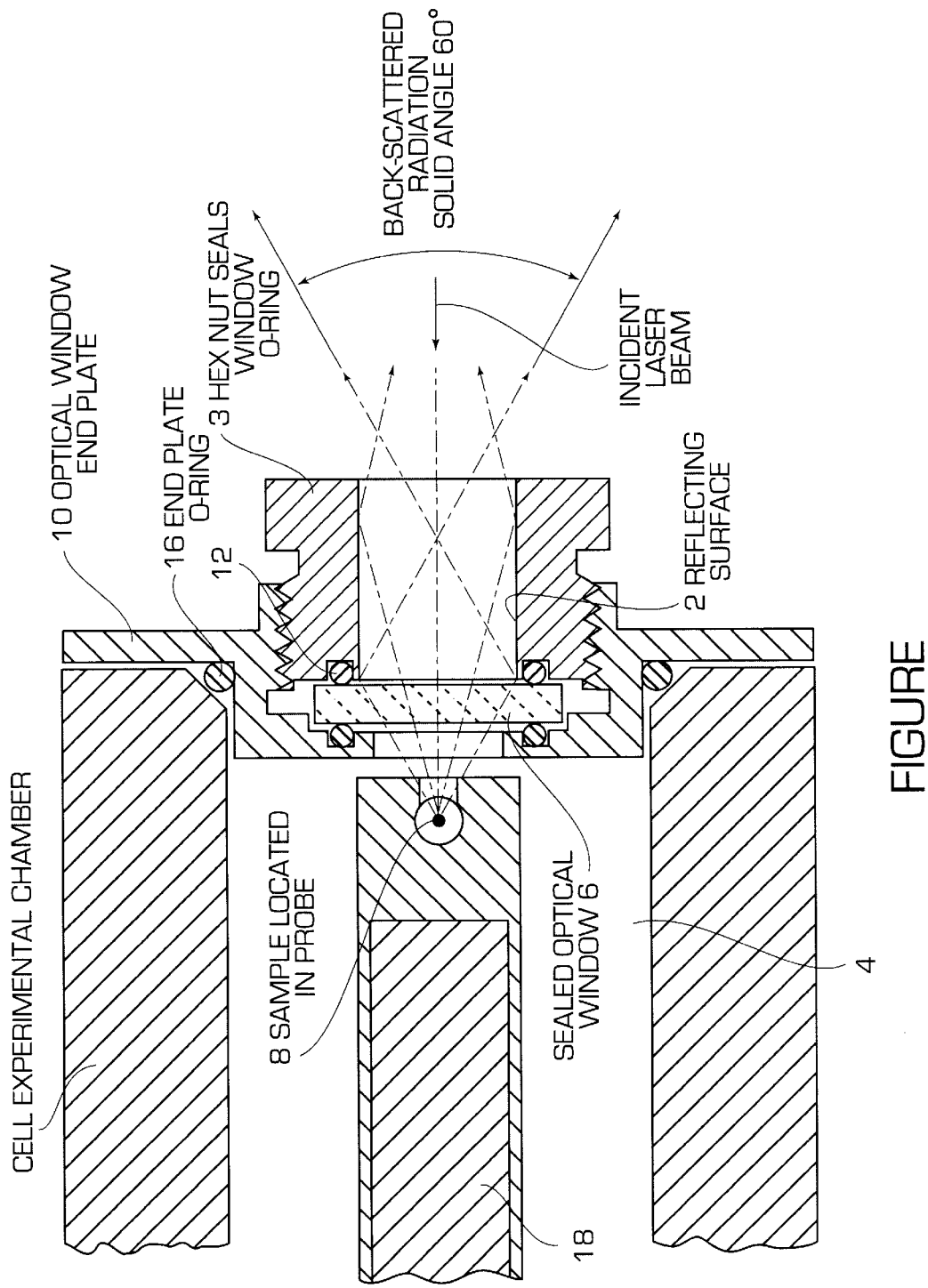
FIGURE

OPTICAL ENERGY TRANSFER METHOD

This is an application based upon Provisional application No. 60/021,521 filed Jul. 10, 1996.

BACKGROUND OF THE INVENTION

1. Field of the Invention

This invention relates to a method and apparatus for transferring energy from one optical system to another. In particular, the invention relates to a method and apparatus for correcting optical mismatch and avoiding the necessity of using complex mirror or lens systems.

2. Background

In many situations it is necessary to transfer efficiently optical radiation from one system to another. While this can be achieved by proper design of optical interfacing systems (lenses, mirrors, etc), in some cases, such conventional interfacing is not always possible or desirable, for example, because of space limitations.

Such a situation can arise, for example, in the case of Raman Spectrophotometers. Here the sample may be irradiated by means of a laser source and the scattered radiation from the sample is then collected (by a mirror, for example) and re-focused into the spectrophotometer optical system. In the case of simple samples, the focal length of the collecting optics may be quite short and a large angle (for example, 60 to 90 degrees) for collection can be obtained with modestly sized mirrors. However, in more complex sampling situations, the sample handling equipment may itself be quite large and it may be impossible to bring the sample to the optimal location (the focal point of the collecting mirror). In such situations, additional conventional optics would be required or the collecting mirror would have to be replaced with one of larger focal length and substantially larger physical size or a mirror with a much reduced angle of collection for the radiation.

SUMMARY OF THE INVENTION

The invention relates to a method of collecting optical energy including the steps of directing optical energy onto a sample, and using the internal hollow surface of a solid member to collect optical energy scattered, reflected or otherwise emanating from the sample. In this manner, the reflecting internal surface of the hollow solid member is used to transfer optical energy from one location to another.

According to another aspect of the invention a plurality of internal surfaces of a plurality of solid members are used to collect and transfer optical energy from one location to another.

Using the method of the present invention, optical energy is transferred from a large sample handling system to an optical spectrophotometer. More particularly, according to the invention, the optical energy is transferred from one optical system to another optical system.

Further, more than one hollow member may be disposed on either side of an optical window or distributed through an optical system. The internal diameter of the hollow member varies over its length and the internal diameters of different hollow members are different from each other.

The optical energy is divergent radiation that is transferred to and collected by a relatively small mirror or lens system with a short focal length.

BRIEF DESCRIPTION OF THE DRAWING

FIG. 1 is a cross-sectional view of the apparatus used in a preferred embodiment of the invention.

DETAILED DESCRIPTION OF A PREFERRED EMBODIMENT OF THE INVENTION

The invention allows the use of short focal length mirrors of relatively small physical size and in particular the use of the standard collecting mirrors usually employed in such spectrophotometers, for a wide range of sample sizes and collection configurations.

In a preferred embodiment of the invention illustrated in the figure, a relatively large diameter internally coated surface 2 of member, which in many cases can be incorporated into the design of other elements in the sampling system, is used. A physically large cell 4 (for example, a cell providing variable temperature and variable pressure spectroscopy) can be interfaced easily to a radiation collector, such as a mirror. In this case the member 3 sealing the end window on the cell is internally coated (with gold in the preferred embodiment) to constitute surface 2 and this acts as a transfer mechanism for the back-scattered radiation from sample 8. The preferred embodiment provides a solid collecting angle of 60 degrees from the sample and transfers this energy to the standard radiation collector, such as a collecting mirror, of the spectrophotometer. Specifically, radiation, such as laser light, incident upon the sample 8 is backscattered through the window 6, reflects off of internal surface 2, and falls incident on a collecting mirror, or the like.

With reference to the figure, the member 3 has external threads which are threadedly engaged with threads provided on an optical window end plate 10. Sandwiched between the member 3 2 and the end plate 10 is the optical window 6 which is sealed by O-rings 12 and 14. The end plate 10 is secured by any suitable means to the cell 4 in a sealed manner using O-ring 16. A probe 18 is provided inside the cell 4 for retaining the sample 8, as shown.

In a modification of the preferred embodiment, the internal bore of a tube (circular or otherwise) can be advantageously used to provide reflecting surfaces on either or both sides of the window 6 (or window system) to effect the transfer of optical energy. In the case of two or more tubes, the diameters of the respective tubes need not be the same as each other and the diameters can even vary along the length of each tube.

An advantage of this modification is that the same arrangement of an optical transfer system will suit a variety of collecting optics, with perhaps only a slight movement in relative separation of cell and collecting mirror being required to provide optimization for various focal lengths and angles of collection with the original collecting optics. Such adjustment of relative spacing is easily provided by simple alignment slides fitted to the cell (or apparatus) or by other conventional methods for positional adjustment.

While a preferred embodiment is disclosed herein, it will be apparent to those of skill in the art that various modifications can be made without departing from the scope of the invention.

What is claimed is:

1. A method of collecting optical energy comprising:
   directing optical energy onto a sample;
   using the internal surface of a hollow member to collect optical energy scattered, reflected or otherwise emanating from the sample; and
   positioning the hollow member, remote from the sample.
2. A method according to claim 1, wherein the internal surface of the hollow member is used to transfer optical energy from one location to another.

3. A method according to claim 1, wherein said using step comprises collecting and transferring optical energy from one location to another with a plurality of hollow members having said internal surface.

4. A method according to claim 1 wherein the optical energy is transferred from a large sample handling system to an optical spectrophotometer.

5. A method according to claim 1 wherein the optical energy is transferred from one optical system to another optical system.

6. A method according to claim 3, wherein at least one of said hollow members is disposed on each side of an optical window.

7. A method according to claim 3 wherein the internal diameter of the hollow member varies over its length and where the internal diameters of different hollow members are different from each other.

8. A method according to claim 1 wherein said optical energy is divergent radiation that is transferred to and collected by a relatively small mirror or lens system with a short focal length.

9. A method according to claim 3 where the internal diameters of said plurality of hollow members are different from each other and work cooperatively together to transfer optical energy.

* * * * *